United States Patent [19]

Paul et al.

[11] 4,048,167
[45] Sept. 13, 1977

[54] N,N-DISUBSTITUTED DERIVATIVES OF 3-CARBOXAMIDE OR 3-THIOCARBOXAMIDE-7-(3-CHLORO-2-PROPENYL)-1,3,5,7-TETRAAZABICYCLO(3.3.1)NONANE AND PREPARATION II

[75] Inventors: Albertha M. Paul, Holliston, Mass.; Charles E. Moppett, Mystic, Conn.

[73] Assignee: The Dow Chemical Company, Midland, Mich.

[21] Appl. No.: 741,090

[22] Filed: Nov. 11, 1976

[51] Int. Cl.$^2$ .................. C07D 257/10; C07D 519/00
[52] U.S. Cl. ..................................... 544/215; 424/249
[58] Field of Search ................................. 260/248 NS

[56] References Cited
U.S. PATENT DOCUMENTS 3,862,187   1/1975   Mitchell et al. ............... 260/248 NS Primary Examiner—John M. Ford
Attorney, Agent, or Firm—Theodore Post; C. Kenneth Bjork

[57] ABSTRACT

Compounds of the formula

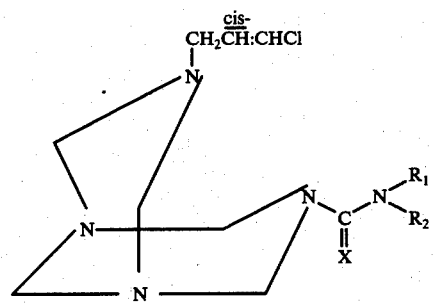

where X represents O or S and $R_1$ and $R_2$ each represents lower alkyl, phenyl or (lower alkyl)phenyl. The compounds are prepared by reacting the ring-opened intermediate (obtained by reacting cis-1-(3-chloro-2-propenyl)-3,5,7-triaza-1-azoniatricyclo(3.3.1.1$^{3,7}$)decane chloride with excess aqueous sodium hydroxide) with an equivalent amount of a corresponding carbamoyl halide or thiocarbamoyl halide or at a low temperature to give the indicated tetrasubstituted urea or thiourea product. The compounds have antimicrobial utility.

7 Claims, No Drawings

N,N-DISUBSTITUTED DERIVATIVES OF 3-CARBOXAMIDE OR 3-THIOCARBOXAMIDE-7-(3-CHLORO-2-PROPENYL)-1,3,5,7-TETRAAZABICYCLO(3.3.1-)NONANE AND PREPARATION II

SUMMARY OF THE INVENTION

This invention concerns novel N,N-disubstituted derivatives of 3-carboxamide and 3-thiocarboxamide-7-cis-(3-chloro-2-propenyl)-1,3,5,7-tetraazabicyclo-(3.3.1)nonane corresponding to the formula

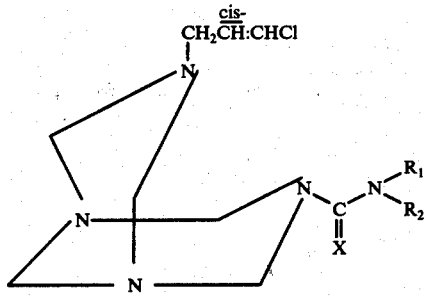

wherein X represents O or S and $R_1$ and $R_2$ each represents lower alkyl, phenyl or (lower alkyl)phenyl. The compounds are all odorless, white, crystalline solids, readily soluble in common organic solvents.

In the specification and claims, the term "lower alkyl" designates an alkyl group having from 1, to 2, to 3, to 4 carbon atoms, for example, methyl, ethyl, propyl or butyl. The term "halo" designates chloro or bromo.

The compounds are prepared in a process wherein cis-1-(3-chloro-2-propenyl)-3,5,7-triaza-1-azoniatricyclo (3.3.1.1$^{3,7}$)decane chloride, commercially available as Dowicil(R) 200 antimicrobial is treated with excess aqueous sodium hydroxide to give the ring-opened intermediate, hereinafter "basic oil," as follows:

Dowicil(R) 200 + NaOH → basic oil

Excess sodium hydroxide, preferably, 4 molar proportions, is dissolved in water and cooled to room temperature. A quantity of about one mole of Dowicil(R) 200 antimicrobial is added slowly to the caustic solution and the reaction mixture is stirred approximately 15 minutes at ambient temperature. The basic oil which forms is extracted with benzene, the extract is dried over sodium sulfate and the benzene is evaporated to give the basic oil in an approximately 78% yield as a viscous oil.

The products of this invention, hereinafter referred to as the Compounds or the Compound, are prepared by reacting the basic oil with an equivalent amount of a carbamoyl or thiocarbamoyl halide in the presence of an acid acceptor, preferably a tertiary amine, according to the following scheme:

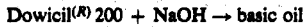

Basic oil + Cl—C=X(NR$_1$R$_2$) $\xrightarrow{Et_3N}$

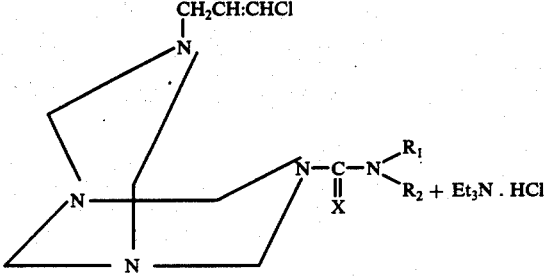

In the equation, X, $R_1$ and $R_2$ have the designations previously given.

In practice, the carbamoyl or thiocarbamoyl halide is dissolved in an inert, anhydrous non-nucleophilic solvent such as acetone, ether, benzene, diglyme, tetrahydrofuran or petroleum ether and added in any excess to a solution of the basic oil in a similar solvent at about 0° C in the presence of an acid acceptor, most advantageously a tertiary amine, in at least an amount equivalent to the carbamoyl or thiocarbamoyl chloride. The reaction is completed in a matter of minutes. The acid acceptor salt precipitates out, is removed from the reaction medium and solvent is evaporated to leave an oil residue. White crystalline Compound is obtained by adding benzene to the oil and separating the crystals. Compound is identified by elemental analysis and by nuclear magnetic resonance.

DESCRIPTION OF SOME PREFERRED EMBODIMENTS

The following examples and teachings additionally describe specific embodiments and the best mode contemplated by the inventors of carrying out the invention.

Example A:

Preparation of Basic Oil Intermediate

A quantity of 80 g (2.0 mole) of NAOH was dissolved in 500 ml water and cooled to room temperature. 100 Grams (0.4 mole) of Dowicil(R) 200 antimicrobial was added slowly to the caustic solution and the reaction mixture stirred ca. 15 minutes at ambient temperature. Extraction of the reaction medium with benzene, drying over Na$_2$SO$_4$ and evaporation of the benzene gave 72 g (78% yield) of the basic oil, described above, as a viscous oil.

Example 1:

N,N-Dimethyl-3-Carboxamide-7-cis-(3-Chloro-2-Propenyl)-1,3,5,7-Tetraazabicyclo(3.3.1)Nonane 10.0 Grams (0.043 mol) basic oil was dissolved in 50 ml dry ether and filtered through Celite(R). 4.35 Grams (0.043 mol) freshly distilled triethylamine (phenyl isocyanate was added to the distillation flask to remove primary and secondary amines) was dissolved in 50 ml dry ether and added to the basic oil solution. The mixture was cooled to 0° C and 4.62 (0.043 mol) dimethylcarbamoyl chloride dissolved in 25 ml ether was added slowly to the cold basic oil-triethylamine solution while stirring. A white precipitate formed immediately and the reaction was complete in 15 minutes. The precipitate, identified by NMR as Et$_3$N.HCl salt, was filtered from the reaction mixture. The filtrate was evaporated on a rotary evaporator to give ~10 g of an oily residue (~85% yield). White crystals, obtained by addition of benzene to the oil, were identifited by NMR and elemental analysis as the titular product. M.P. 173°–6° C.

Example 2:

The same procedure was followed for all following Compounds:

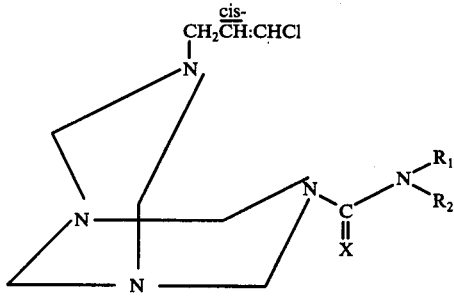

a. $R_1 = R_2 = C_2H_5$, X = O, m.p. 160–3° C
b. $R_1 = R_2 = C_6H_5$, X = O, m.p. 128–30° C
c. $R_1 = CH_3$, $R_2 = C_6H_5$, X = O, m.p. 103–5° C
d. $R_1 = R_2 = CH_3$, X = S, m.p. 145–7° C

All Compounds of the invention are useful as antimicrobials for the control of bacteria and fungi. This is not to suggest that the Compounds and their mixtures are equally effective against all such organisms at the same concentration. For such uses the Compounds or their mixtures can be employed in an unmodified form or dispersed in water with the aid of a surface-active agent, and the resulting emulsions employed as sprays. In other procedures, the products can be employed as active constituents in solvent solutions, oil-in-water or water-in-oil emulsions, including cosmetic emulsions. The augmented compositions are adapted to be formulated as concentrates and subsequently diluted with additional liquid or solid adjuvant to produce the ultimate treating compositions. Good results are obtained when employing compositions containing antimicrobial concentrations and usually from about 100 to about 1,000 parts by weight of one or more of the Compounds per milliom parts of such compositions.

Incorporation of the Compounds of this invention into materials which are subject to bacterial and/or fungal attack inhibits the growth of such microbes and preserves the original value of the materials. The Compounds are sufficiently non-volatile and water-insoluble that they will persist on or in such materials for long periods of time. Examples of materials which are adversely affected by fungal growth are latex paint films, wood and wooden products. The inventive compounds are sufficiently active against fungi that only small quantities are required to prevent mildew on paint films or wood rot. The Compounds are therefore useful for long-term protection against fungal growth in or on materials having a wood basis or a protective or decorative paint film subject to fungal attack.

In representative operations, the products of the invention, when tested for antimicrobial activity using conventional agar Petri dish dilution tests, showed the following minimum inhibitory concentrations in parts per million against the following organisms:

| Cpd. of Example | MIC, ppm | | | | | | | |
|---|---|---|---|---|---|---|---|---|
| | Sa* | Ec* | Tm* | Bs* | Aa* | St* | Ps* | Mp* |
| 1 | 500 | 500 | 100 | 100 | 100 | 100 | 500 | 500 |
| 2 a. | 500 | 100 | 100 | 100 | 100 | 100 | 100 | 500 |
| 2 b. | 500 | 500 | 100 | 500 | 500 | 100 | 500 | 500 |
| 2 c. | 500 | 500 | 100 | 500 | 500 | 100 | 500 | 500 |
| 2 d. | 500 | 500 | 100 | 100 | 500 | 100 | 500 | 500 |

*Sa = *S. aureus*
Ec = *E. coli*
Tm = *mentagrophytes*
Bs = *B. subtilis*
Aa = *A. aerogenes*
St = *S. typhosa*
Ps = *Pseudomas Species* Str. 10
Mp = *M. phlei*

What is claimed is:

1. A compound corresponding to the formula

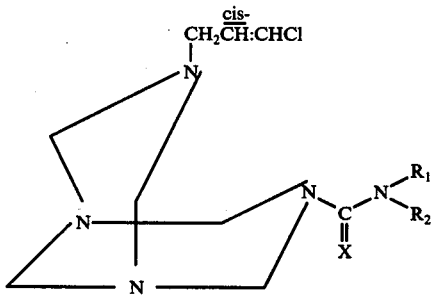

wheren X represents O or S and $R_1$ and $R_2$ each represents lower alkyl, phenyl or (lower alkyl)phenyl.

2. The compound of claim 1 wherein X represents O and $R_1$ and $R_2$ both represent methyl.

3. The compound of claim 1 wherein X represents O and $R_1$ and $R_2$ both represent ethyl.

4. The compound of claim 1 wherein X represents O and $R_1$ and $R_2$ both represent phenyl.

5. The compound of claim 1 wherein X represents O, $R_1$ represents methyl and $R_2$ represents phenyl.

6. The compound of claim 1 wherein X represent S and $R_1$ and $R_2$ both represent methyl.

7. Method for making an N,N-disubstituted derivative of 3-carboxamide- or 3-thiocarboxamide-7-cis-(3-chloro-2-propenyl)-1,3,5,7-tetraazabicyclo-(3.3.1)nonane by mixing together at about 0° C until reaction is substantially complete substantially equivalent proportions of (1) a carbamoyl or thiocarbamoyl halide having the formula hal-C=X(NR$_1$R$_2$) wherein hal is Cl or Br, X is O or S and $R_1$ and $R_2$ each is lower alkyl, phenyl or (lower alkyl)phenyl dissolved in an organic non-nucleophilic solvent and (2) the reaction product of Dowicil(R) 200 with excess aqueous sodium hydroxide at a reaction temperature between about minus 15° and about 5° C, also in solution in a similar solvent, in the presence of an acid acceptor, and recovering the said product.

* * * * *